United States Patent [19]

Kikuchi et al.

[11] Patent Number: 4,478,937
[45] Date of Patent: Oct. 23, 1984

[54] PLASMID AND PRODUCTION THEREOF

[76] Inventors: Masakazu Kikuchi, 4-16, Higashitokiwadai 7-chome, Toyono-cho, Toyono-gun, Osaka, Japan, 563-01; Takaki Hayakawa, 6-31, Zuiko 1-chome, Higashiyodogawa-ku, Osaka, Japan, 533; Makoto Kida, 138-3, Aza-midorigaoka, Yamahara, Kawanishi, Hyogo, Japan, 666-01

[21] Appl. No.: 370,273

[22] Filed: Apr. 20, 1982

[30] Foreign Application Priority Data

Apr. 28, 1981 [JP] Japan ................... 56-64369

[51] Int. Cl.³ ............ C12N 15/00; C12N 1/00; C12N 1/20; C12P 21/00; C12P 19/34
[52] U.S. Cl. ................... 435/172.3; 435/317; 435/68; 435/91; 435/253; 935/16; 935/29; 935/72; 935/74; 935/75
[58] Field of Search ........... 435/68, 70, 172, 253, 435/317, 867, 91, 172.3

[56] References Cited

U.S. PATENT DOCUMENTS 4,273,875 6/1981 Manis .
4,360,597 11/1982 Bibb et al. ................. 435/172

FOREIGN PATENT DOCUMENTS 0038156 10/1981 European Pat. Off. ......... 435/172
0039099 4/1981 Japan ........................ 435/172
2044773 10/1980 United Kingdom ............ 435/172

OTHER PUBLICATIONS

Helling et al.: in *Genetic Engineering*, Chakrabarty (ed.), CRC Press, 1978, pp. 1–30.
American Type Culture Collection Catalog (ATCC), Thirteenth Ed., 1978, p. 98.
Bagdasarian et al.: in *Plasmids of Medical Environmental and Commercial Importance*, Timmis et al. (ed.), Elsevier/Norh Holland, 1979, pp. 411–422.
Eichenlaub et al.: in *Plasmids of Medical, Environmental and Commercial Importance*, Timmis et al. (ed.), Elsevier/North Holland, 1979, pp. 423–432.
Mukai et al.: Molec. Gen. Genet., 146, 269 (1976).
Tanaka et al.: J. Bacteriol., 129, 1487 (1977).
Gunge et al.: J. Bacteriol., 145, 382 (1981).
Novick: J. Bacteriol., 127, 1177 (1976).
Szybalski et al.: Gene 1, 217 (1979).
Bibb et al., Nature, 274: 398 (1978).
Helling et al., J. of Virology, 14: 1235 (1974).
Murray et al., J. Mol. Biol., 98: 551 (1975).
Cohen, Scientific American, 233: 24 (1975).
Kleinschmidt, Methods in Enzymology, 12: 361 (1968).
Chater et al., Current Topics in Microbiology and Immunology, 96: 69 (Springer Verlag, 1982).

*Primary Examiner*—Lionel M. Shapiro
*Assistant Examiner*—James Martinell
*Attorney, Agent, or Firm*—David G. Conlin

[57] ABSTRACT

A novel plasmid pATM2 is obtainable from a microorganism belonging to the genus Micromonospora. The plasmid pATM2 is useful as a cloning vector in recombinant DNA work.

5 Claims, 1 Drawing Figure

PLASMID AND PRODUCTION THEREOF

This invention relates to a novel plasmid and a process for producing the same.

With the recent progress in recombinant DNA (deoxyribonucleic acid) research using microorganisms, great efforts have been made to develop useful vectors capable of being introduced into bacteria, e.g. *Escherichia coli*. On the other hand, actinomycetes are capable of producing a variety of antibiotics and physiologically active substances, and have been valued highly for a long time in the field of fermentation. However, only a very limited number of techniques are available for breeding actinomycetes, and large amounts of time and labor required constitute obstacles to pursuance of such research. Therefore, it has been desired to elaborate host-vector systems which enable recombinant DNA research as a means for bringing about improvement in breeding of actinomycetes, and accordingly several plasmids have been found and trial use thereof as vectors has been conducted. In such trial use, strains of the genus Streptomyces have been used.

The present inventors, through their researches to develop a recombinant DNA technology in strains belonging to the genus Micromonospora which are capable of producing chemotherapeutically useful antibiotics such as aminoglycoside and macrolide antibiotics, have found that a novel plasmid can be obtained from said microorganism, and have completed the present invention based on that finding.

Thus this invention provides (1) certain plasmids which are useful, e.g., as cloning vectors in genetical production methods, e.g., where desired genes are incorporated into the plasmid, the plasmid is transformed into a suitable host, and the host utilized to produce desired product(s). A preferred plasmid in accordance with the invention is a plasmid pATM2 (hereinafter sometimes referred to as "pATM2" for short), having a molecular weight of about 4.87±0.05 megadaltons and characterized by certain restriction endonuclease cleavage sites described below. And this invention provides also (2) a method for producing a plasmid which comprises cultivating a plasmid-harboring microorganism belonging to the genus Micromonospora in a culture medium, harvesting cells therefrom, subjecting said cells to lysis, and isolating the plasmid from the lysate.

BRIEF DESCRIPTION OF THE DRAWING

The drawing depicts the restriction endonuclease cleavage map for plasmid pATM2, constituted on the basis of plasmid pATM2 having a molecular weight of about 4.9 megadaltons. The map positions of the various restriction endonuclease cleavage sites are given as megadalton coordinates relative to the EcoRI cleavage site at 0.0/4.9 megadaltons.

As the plasmid-harboring microorganism belonging to the genus Micromonospora usable in the practice of this invention, there may be mentioned *Micromonospora coerulea*, and more specifically *Micromonospora coerulea* IFO 13504 (ATCC 27008). The last-mentioned microorganism was deposited on Nov. 30, 1972 at Institute for Fermentation, Osaka (IFO), Japan under the accession number of IFO 13504, is listed in Institute for Fermentation, Osaka, List of Cultures, Sixth Edition, 1978, and is stored at said institute. The microorganism is also listed in The American Type Culture Collection, Catalogue of Strains I, Fourteenth Edition, 1980 under the accession number of ATCC 27008.

Figure 1:
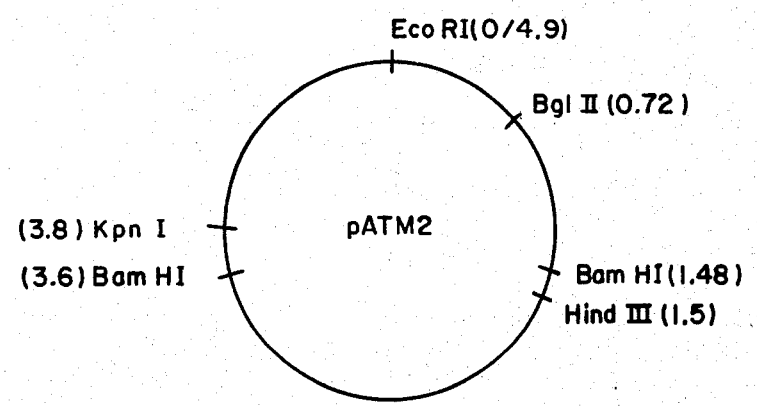

The culture medium to be used in the practice of this invention may be any of those culture media in which a microorganism in accordance with this invention can grow and retain the plasmid in cells thereof. The carbon source to be contained in said medium is, for example, glucose, sucrose, glycerol, starch, dextrin, molasses, or an organic acid. The nitrogen source to be contained in said medium is such an organic nitrogen source as peptone, meat extract, yeast extract, Casamino Acids (Difco, U.S.A.), NZ-Amine A (Sheffield, U.S.A.), soybean meal, or peanut meal, or such an inorganic nitrogen source as ammonium sulfate, ammonium chloride, or ammonium nitrate. In addition, such inorganic salts as calcium salts, magnesium salts, potassium salts, sodium salts, phosphoric acid salts, manganese salts, iron salts or cobalt salts may be added to the medium when necessary. For auxotrophic strains, the nutrients required for their growth may be added to the medium. Examples of such nutrients are amino acids, vitamins, and nucleic acid bases.

Furthermore, an antifoaming agent (e.g. soybean oil, lard oil) and other agents may be added to the medium when necessary.

If necessary at the time of incubation, an antibiotic, such as chloramphenicol, may be added to the medium.

The incubation temperature is generally about 15°–42° C., preferably about 24°–35° C., and the initial pH of the medium is generally about 6.0–8.0, preferably about 6.5–7.5. The incubation period is generally about 2–8 days, preferably about 2–4 days.

The mycelia grown by the above-mentioned incubation are collected and lysed, and the plasmid is recovered from the lysate. Harvesting the cells may be carried out by a per se known method, such as centrifugation or filtration.

For cell lysis of strains of the genus Micromonospora, there may be mentioned, for example, the use of a lytic enzyme (e.g. lysozyme). If necessary, the lysis may be facilitated by addition of such an enzyme as protease or a surfactant as Sarcosyl (sodium N-lauroylsarcosinate; a product of Wako Pure Chemical Industries, Ltd., Japan) or sodium lauryl sulfate in addition to the lytic enzyme, and/or by freezing and thawing.

Recovery of the plasmid from the lysate thus obtained can be achieved by methods known per se, for instance, by an appropriate combination of DNA precipitation with ethanol, ethidium bromide-containing cesium chloride density gradient centrifugation, sucrose density gradient centrifugation, affinity chromatography, hydroxyapatite chromatography, gel electrophoresis, cellophane membrane dialysis, etc.

The present plasmid pATM2 as obtained in Example 1 mentioned hereinbelow has cleavage sites for a variety of restriction endonucleases. The cleavage map of pATM2 is shown in FIG. 1. Said restriction endonuclease cleavage map has been constructed based on the fact that the plasmid pATM2 is circular, the molecular weight of pATM2 is approximately 4.9 megadaltons and the cleavage sites for restriction endonucleases are as follows:

Eco RI (0/4.9)
Bgl II (0.72)
Bam HI (1.48 and 3.6)
Hind II (1.5)
Kpn I (3.8)

The sensitivities of pATM2 against several restriction endonucleases are as follows:

| Number of restriction endonuclease cleavage sites in pATM2 | | | |
|---|---|---|---|
| Restriction endonuclease | Number of cleavage sites | Restriction endonuclease | Number of cleavage sites |
| Bam HI | 2 | Eco RI | 1 |
| Bgl II | 1 | Hind III | 1 |
| Kpn I | 1 | Sma I | $\geq 3$ |
| Sal I | $\geq 3$ | Xho I | 0 |

The above results were obtained by digesting the pATM2 DNA with an excess of each restriction endonuclease. Each number of cleavage sites as shown was determined based on the number of fragments which could be separated by agarose gel [either 1.2% (w/v) or 1.5% (w/v)] electrophoresis.

The restriction endonucleases used were as follows:
(1) Eco RI is a restriction endonuclease isolated from *Escherichia coli* RY13(R1);
(2) Bgl II is one from *Bacillus globigii;*
(3) Bam HI is one from *Bacillus amyloliquefaciens;*
(4) Hind III is one from *Haemophilus influenzae;*
(5) Kpn I is one from *Klebsiella pneumoniae* OK8;
(6) Sma I is one from *Serratia marcescens* Sb;
(7) Xho I is one from *Xanthomonas holcicola;* and
(8) Sal I is one from *Streptomyces albus* G.

The above restriction endonucleases are available from Takara Shuzo Co., Ltd. (Japan) or New England Biolabs, Inc. (USA).

The molecular weight of pATM2 can be determined by methods known per se, such as electron microscopy, and restriction endonuclease digestion followed by agarose gel electrophoresis.

The plasmid provided by the present invention has cleavage sites for a variety of restriction endonucleases, and thus a number of useful vectors can be developed by modifying this plasmid. It is also possible to insert a desired gene into this plasmid or a derivative thereof and introduce the recombinant plasmid into a host microorganism by transformation. In particular, the plasmid of this invention can advantageously be used as a vector for the stable maintenance of foreign DNA in those microorganisms that are of importance in the fermentation industry, for example, actinomycetes. Thus, cloning of genes from actinomycetes by the use of the plasmid of the invention, followed by introduction of the cloned information into an adequate microorganism, may lead, for example, to increased production of antibiotics, physiologically active substances, enzymes and other secondary metabolites by actinomycetes.

The plasmid in accordance with the invention can be used as a vector for cloning not only genes of microorganisms but also genes of higher animals and plants (for example, genes coding for somatostatin, insulin etc., or genes involved in nitrogen fixation).

In such use, the method of preparing a recombinant plasmid containing a desired gene is known per se, and is described, for example, in Scientific American, vol. 233, No.1, pages 24–33 (1975), which is hereby incorporated by reference.

The method of introducing the recombinant plasmid thus obtained into a host is also known per se, and is described, for instance, in Nature, vol. 274, pages 398–400 (1978), which is hereby incorporated by reference.

As pATM2 is a small plasmid, pATM2 is advantageously used in the recombinant DNA research.

The desired substance can be produced by growing in a manner known per se a host microorganism with a therein-incorporated plasmid with a gene inserted therein by using the plasmid of the invention as a vector, which gene is necessary for the biosynthesis of the desired substance, and recovering and purifying the desired substance formed and accumulated in the culture medium or in cells.

A perhaps more useful approach is to introduce a plasmid vector, e.g. pATM2, into a host which normally produces the product, and to clone onto the plasmid the genes for biosynthesis of the product. In this way, problems of fermentation and product extraction and purification are minimized. Additionally, in this cloning system it may not be necessary to clone and amplify all the genes of the biosynthetic pathway, but rather it may be necessary only to clone regulatory genes or genes coding for the enzymes that are rate limiting in product biosynthesis.

The plasmid of the present invention, being a plasmid of actinomycetes, not only can be used in systems in which the host is an actinomycete but also may be used as a vector in systems in which the host is some other grampositive bacterial strain, such as one belonging to the genus Bacillus, Corynebacterium or Brevibacterium.

The following example illustrates the invention in more detail but should by no means be construed as limitative of the invention. Unless otherwise stated, "percent (%)" means "weight/volume percent (w/v %)."

EXAMPLE 1

Isolation of plasmid pATM2 from *Micromonospora coerulea* IFO 13504.

Ten ml of a liquid medium (pH 7.3) containing 0.4% Bacto yeast extract (Difco, U.S.A.), 1% Bacto malt extract (Difco, U.S.A.) and 0.4% glucose were dispensed in a large test tube (20 mm$\phi \times$245 mm). After sterilization, the medium was inoculated with *Micromonospora coerulea* IFO 13504 and incubated at 28° C. for 6 days with shaking. The whole culture was transferred to a sterilized 400-ml portion of the medium of the same components as above in a 2-liter Sakaguchi flask, and incubated on a reciprocal shaker at 28° C. for 3 days. The culture was centrifuged at 8,000 revolutions per minute (rpm) for 10 minutes. The mycellia collected were washed twice with TES buffer [containing 30 mM tris-hydroxymethylaminomethane, 5 mM EDTA (sodium salt of ethylenediaminetetraacetic acid)and 50 mM NaCl; pH 8.0]. The wet cells (15.7 g) thus obtained were suspended in TES buffer so as to give a homogeneous suspension. The suspension was adjusted to 0.9 at OD$_{600}$ with TES buffer. Thereto were added 240 ml of 25% sucrose solution (in TES buffer), 40 ml of 0.25 M EDTA solution (pH 8.0), 80 ml of lysozyme solution (5 mg of lysozyme, product of Seikagaku Kogyo, Japan, per ml of 25% sucrose solution as mentioned above); and 8 ml of RNase (Ribonuclease) A-1 (Sigma, U.S.A.) solution (preliminarily heat-treated at 100° C. for 10 minutes; RNase A-1 concentration 5 mg/ml). After adequate mixing, the mixture was maintained at 37° C. for an hour with occasionally gentle stirring. To the resulting reaction mixture, there was added 10% Sarcosyl solution [solution of Sarcosyl in TES buffer], and, after mixing, the mixture was kept at the same temperature for an additional hour. Then, 40 ml of Pronase P (Kaken Kagaku Kogyo, Japan) solution (preliminarily autolysed at 37° C. for 30 minutes; Pronase P concentration 5 mg/ml) was added, and the reaction was allowed to proceed at 37° C. for further one hour. Thereafter, 64 ml of 10% SDS solution [solution of sodium dodecyl sulfate (Wako Pure Chemical Industries, Japan) in water] and 136 ml of 5M NaCl were added, and the mixture, after adequate blending, was allowed to stand at 0° C. overnight. The solution was centrifuged at 10,000 rpm for 40 minutes, the supernatant was collected, twice the volume of cooled ethanol was added to the supernatant, and the mixture was allowed to stand at −20° C. overnight and then centrifuged at 10,000 rpm for 30 minutes, to give a precipitate. After completely removing the remaining ethanol, the precipitate was dissolved in 40 ml of 0.4% Sarcosyl solution (in TES buffer). To the solution were added solid cesium chloride and 1.5 ml of ethidium bromide solution (in dimethyl sulfoxide; concentration 30 mg/ml) to the density of 1.600, and the solution was centrifuged in a Beckmann (U.S.A.); 50Ti rotor at 38,000 rpm for 40 hours at 20° C. After centrifugation, the plasmid band was detected as a fluorescent band under ultraviolet light (302 nm). This band was collected by fractionation and subjected again to ultracentrifugation under the same conditions as above. The plasmid fraction thus obtained was mixed with an equal volume of n-butanol with gentle stirring for extractive removal of ethidium bromide. The aqueous layer obtained was dialyzed three times against a large amount of 0.1×SSC+1 mM EDTA (15 mM NaCl, 1.5 mM sodium citrate dihydrate and 1 mM EDTA; pH 7.4). There was obtained 64 μg of pATM2 as DNA.

Electron microscopy of the DNA molecule was done in order to determine the molecular weight corresponding to the average length of pATM2 with pBR322 as standard [cf. Methods in Enzymology, vol. 12, part B, pages 361–377(1968) Academic Press, New York (U.S.A.) which is hereby incorporated by reference.]. Scores of observations gave values falling within the range of 4.87±0.05 with the average value of 4.87 megadaltons. Separately, single, double, or triple digestion of pATM2 with different restriction endonucleases followed by agarose gel electrophoresis of the DNA fragments obtained and molecular weight determination from the mobility data [cf. Journal of Virology, vol.14, pages 1235–1244(1974) which is hereby incorporated by reference] gave, in ten and odd runs, molecular weight values falling within the range of 4.87±0.05 with the average value of 4.85 megadaltons. All the restriction endonucleases used were products of Takara Shuzo Co., Ltd., Japan, and each digestion reaction was carried out under conditions specified by the supplier. The molecular weight determination was based on the standard mobility pattern for fragments obtained by digestion of λ DNA with Hind III [cf. Journal of Molecular Biology, vol. 98, pages 551–564 (1975), which is hereby incorporated by reference].

The methods of uses of plasmids such as pATM2 are well known in the art (see, e.g., Cohen et al U.S. Pat. No. 4,237,224 and Manis U.S. Pat. No. 4,273,875, both of which are hereby incorporated by reference).

What we claim is:

1. An biologically pure plasmid pATM2 which is obtained from a microorganism belonging to the genus micromonaspora and is characterized by the following properties:
    (1) Molecular weight: approximately 4.87±0.05 megadaltons
    (2) Shape: circular
    (3) Restriction endonuclease cleavage sites: Eco RI (0/4.9), Bgl II (0.72), Bam HI (1.48 and 3.6), Hind III (1.5) and Kpn I (3.8)
    (4) Sensitivity to restriction endonucleases:

| Restriction endonuclease | Number of Cleavage Sites |
|---|---|
| Bam HI | 2 |
| Bgl II | 1 |
| Kpn I | 1 |
| Sal I | ≧3 |
| Eco RI | 1 |
| Hind III | 1 |
| Sma I | ≧3 |

2. A method for producing plasmid pATM2 which comprises cultivating a plasmid pATM2-harboring microorganism belonging to the genus Micromonospora in a culture medium, harvesting the cells thereof, subjecting said cells to lysis, and recovering the plasmid pATM2 from the lysate.

3. A method according to claim 2, wherein the microorganism is *Micromonospora coerulea*.

4. A method according to claim 3, wherein the microorganism is *Micromonospora coerulea* IFO 13504.

5. A host microorganism cell containing a vector, the vector comprising plasmid pATM2, the host microorganism being selected from Streptomyces, Bacillus, Corynebacterium and Brevibacterium.

* * * * *